US00PP17522P2

(12) United States Plant Patent
Anatriello

(10) Patent No.: US PP17,522 P2
(45) Date of Patent: Mar. 27, 2007

(54) POINSETTIA PLANT NAMED 'ATN VR2'

(50) Latin Name: *Euphorbia pulcherrima*
Varietal Denomination: ATN VR2

(75) Inventor: Lucilene Anatriello, Sao Jose do Rio Preto (BR)

(73) Assignee: Athena Mudas, Ltda, São Joséde Rio Preta (BR)

( * ) Notice: Subject to any disclaimer, the term of this patent is extended or adjusted under 35 U.S.C. 154(b) by 7 days.

(21) Appl. No.: 11/220,483

(22) Filed: Sep. 8, 2005

(51) Int. Cl.
*A01H 5/00* (2006.01)

(52) U.S. Cl. ..... Plt./307

(58) Field of Classification Search ..... Plt./307
See application file for complete search history.

*Primary Examiner*—Kent Bell
(74) *Attorney, Agent, or Firm*—Albert O. Cota

(57) ABSTRACT

A new and distinct Poinsettia plant cultivar is disclosed, characterized by medium-sized, deep red bracts, blooming consistently after 7.5 weeks of night-length of 13.5 hours or more, with a post-production longevity of 7 weeks or more.

1 Drawing Sheet

Figure 1:
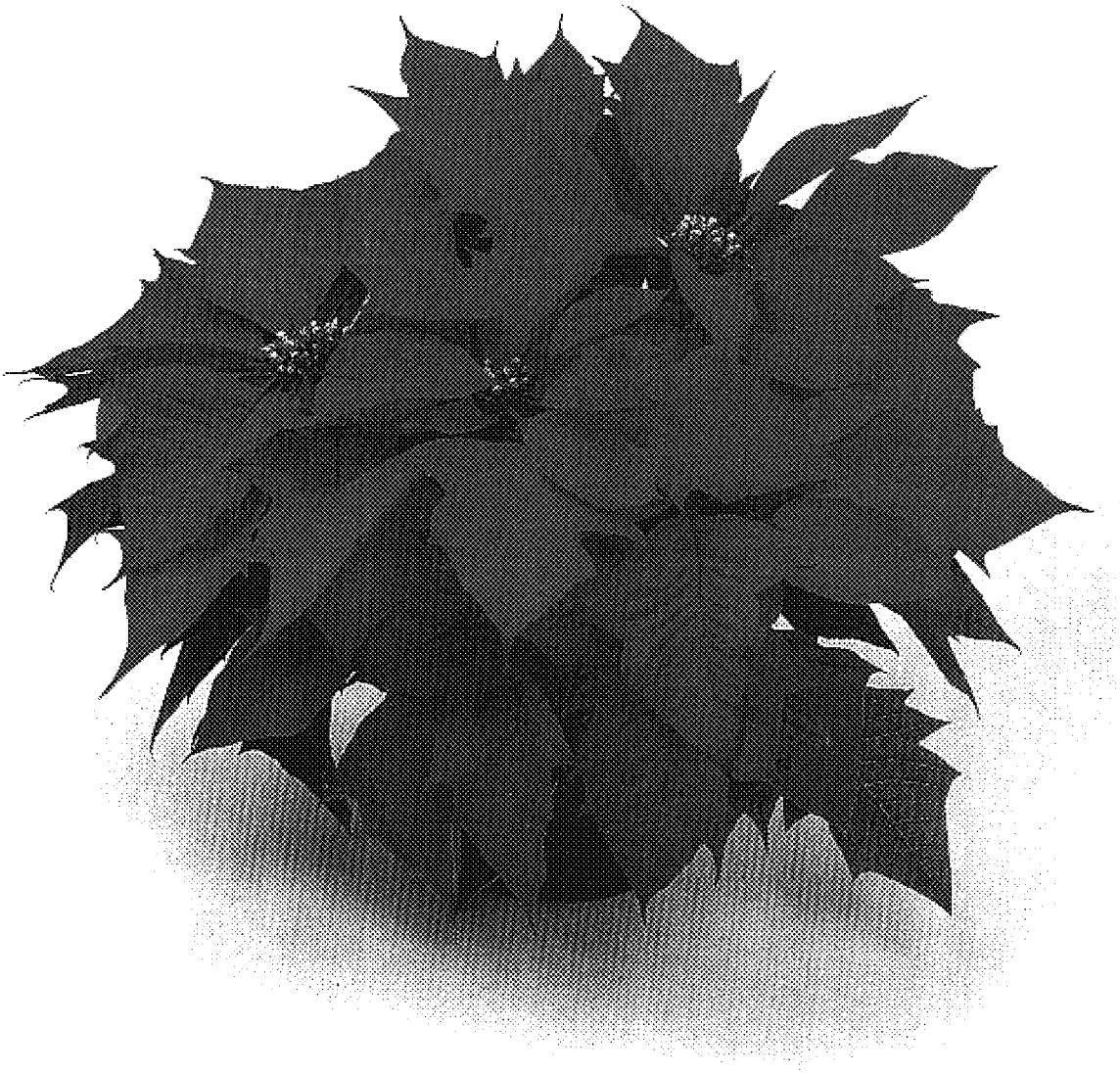

Latin name of the genus and species: *Euphorbia pulcherrima.*

Variety denomination: 'ATN VR2'.

BACKGROUND OF THE INVENTION

The new cultivar 'ATN VR2' is a product of a planned breeding program. The new variety was discovered as a naturally occurring whole plant mutation of the unpatented proprietary seedling 'ATH VEL1' in a planting of more than 3000 pots of 'ATH VEL1'. The new cultivar was discovered and selected as a single plant by Lucilene Anatriello in November 2003.

Asexual reproduction of the new cultivar 'ATN VR2' by terminal cuttings was performed in San Jose Do Rio Petro, Sao Paulo, Brazil, and has shown that the unique features of this new cultivar are stable and reproduced true to type in successive generations.

SUMMARY OF THE INVENTION

The cultivar 'ATN VR2' has not been observed under all possible environmental conditions. The phenotype may vary somewhat with variations in environment such as temperature, daylength, and light intensity, without, however, any variance in genotype.

The following traits have been repeatedly observed and are determined to be basic characteristics of 'ATN VR2' which in combination distinguish this Poinsettia as a new and distinct cultivar:

1. Deep red bract color;
2. Medium sized bracts in tight and flat rosette-like arrangement;
3. Dark-green foliage with moderate lobes;
4. Bracts are medium-sized, v-shaped with the branches slanting upright;
5. Beginning of flowering after 7.5 weeks of night-length of 13.5 hours or more and;
6. Post production longevity of 7 weeks or more.

In comparison to the parental variety 'ATH VEL1', 'ATN VR2' differs in bract coloration.

In comparison to the commercially available variety 'Festival Red' (U.S. Plant Pat. No. 10,253), 'ATN VR2' has different color red bracts as well as different color green foliage. The new variety 'ATN VR2' has smaller bracts in both length and width and additionally, is smaller overall in both plant height and plant spread than 'Festival Red'. Finally, the comparable variety 'Festival Red' has more bracts per inflorescence than the new cultivar 'ATN VR2'.

In comparison to the commercially available variety 'Fismille' (U.S. Plant Pat. No. 13,660), 'ATN VR2' has shorter bracts with more bracts per inflorescence than the comparable variety. The comparable variety 'Fismille' has a distinctly different bract texture than 'ATN VR2' as well as a distinctly different foliage aspect. Finally, the comparable variety has a longer flowering response time than 'ATN VR2'.

BRIEF DESCRIPTION OF THE PHOTOGRAPH

1) The accompanying photograph in FIG. 1 illustrates in full color a typical plant of 'ATN VR2' grown in a 6.5-inch pot. One cutting was used in the pot, planted in late August and grown in a greenhouse using approximately 4,000-foot candles of light. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'ATN VR2' plants grown in Oxnard, Ventura County, Calif., from late August to late November of 2004. The growing temperature ranged from 18° C. to 20° C. at night to 20° C. to 24° C. during the day.

Botanical classification: *Euphorbia pulcherrima* cultivar 'ATN VR2.'

Commercial classification: Poinsettia.

PROPAGATION

Time to initiate rooting: Approximately 10 days at 20–22° C.
Time to develop roots: Sufficiently rooted for transplanting after about 25 days in a greenhouse at temperature of 20–22° C.

PLANT

Form: Mounding inverted triangle self-branching, mounded top of plant.
Growth habit: Moderately compact structure, pinched plants are bushy with the branches upright directed at an angle of roughly 35 degrees, foliage canopy uniformly rounded.
Height: In 6.5 inch pot, approximately 34 cm.
Plant spread: In 6 inch pot, approximately 35 cm.
Growth rate: Low to medium vigor.
Branching characteristics: Free-branching.
Diameter of branches: Approximately 0.9 cm.
Average number of branches: Approximately 7 after pinching.
Length of lateral branches: Approximately 25 cm.
Number of leaves per lateral branch: Approximately 12.
Stem color: Near Green 143A.
Age of plant described: Approximately 30 days.

FOLIAGE

Leaf:
*Arrangement.*—Alternate single.
*Average length.*—Approximately 10 cm.
*Average width.*—Approximately 7 cm.
*Shape of blade.*—Ovate.
*Lobes.*—Moderate lobes.
*Tip.*—Acuminate.
*Base.*—Rounded to almost truncate.
*Attachment.*—Stalked.
*Margin.*—Entire, apart from the lobes.
*Aspect.*—Slightly recurved.
*Texture of top surface.*—Glabrous.
*Texture of bottom surface.*—Glabrous.
*Leaf internode length.*—About 3.2 cm.
*Color.*—Young foliage upper side: Near Yellow-Green 147A. Young foliage under side: Near Green 137B. Mature foliage upper side: Near Green 137A. Mature foliage under side: Near Yellow-Green 147B.
*Venation.*—Type: Pinnate. Venation color upper side: Near Yellow-Green 144B with near Greyed-Orange 176A pigment at base. Venation color under side: Near Green 143C with midrib Red 46A pigment at base.
Petiole:
*Average length.*—Approximately 2.1 cm.
*Color.*—Near Yellow-Green 144B with Greyed-Orange 176A pigment closest to the base.
*Diameter.*—Approximately 0.4 cm.
*Texture.*—Glabrous.
*Aspect.*—Petioles are horizontally directed.

FLOWER

Inflorescence:
*Inflorescence description.*—Inflorescences are compound corymbs of cyathia with colored flower bracts subtending the cyathia. Blooming habit: Begin under natural short day conditions in the fall: Botanically (cyathia open) in late December. Commercially (bracts colored, marketable in late November).
*Flowering response time.*—60 days after beginning of short days (nights longer than 13.5 hours.).
*Flowering description.*—Whole inflorescence with surrounding bracts. About medium-size, star-shaped, with the bracts directed in a tight arrangement and overlapping.
*Natural flowering season.*—Mainly from late November to late December.
*Number of inflorescences per lateral branch.*—Approximately 1.
*Diameter of inflorescence.*—Approximately 12 cm.
*Height of inflorescence.*—Approximately 7 cm.
*Number of bracts per inflorescence.*—About 18.
*Persistence.*—Persistent.
Bracts:
*Length of largest bracts.*—About 6.5 cm.
*Width of largest bracts.*—About 6 cm.
*Keeping quality.*—Plants have a post-production longevity of 7 weeks or more.
*Shape.*—Ovate, with moderate lobes.
*Base.*—Obtuse, moderate lobes with acute tips.
*Terminal tip.*—Acuminate.
Texture:
*Upper surface.*—Glabrous, velvety.
*Lower surface.*—Glabrous velvety.
*Aspect.*—Slightly recurved.
*Venation pattern.*—Pinnate.
Color:
*Developing bracts.*—Upper surface: Near Red 46C. Lower surface: Near Red 45C.
*Mature bracts.*—Upper surface: Near Red 46B. Lower Surface: Near Red 45B.
Bract petiole:
*Length.*—Approximately 2 cm.
*Diameter.*—Approximately 0.4 cm.
*Color.*—Near Red 46C.
Cyathium: About 20 per corymb.
Diameter of cyathia cluster: About 3.4 cm.
Length of individual cyathia: Approximately 1 cm.
Width of individual cyathia: Approximately 0.8 cm.
Shape: Ovoid.
Color:
*Immature.*—Near Yellow 9B.
*Mature.*—Near Yellow-Orange 15A.
Aging: Near Yellow-Orange 21C.
Nectar cups/nectaries:
*Quantity.*—One or two per cyathium.
*Width.*—Up to 5 mm wide.
*Color.*—Near Yellow 9A.
Peduncle:
*Length.*—About 0.3 cm.
*Diameter.*—About 0.2 cm.
*Strength.*—Strong.
*Aspect.*—Upright.
*Texture.*—Glabrous.
*Color.*—Near Yellow-Green 145B.
Reproductive organs:
*Stamens.*—Approximately 15 in a cluster.
*Anther shape.*—Bi-lobed.
*Anther length.*—About 0.1 cm.
*Anther color.*—Near Red 42A.
*Quantity of pollen.*—Moderate.
*Pollen color.*—Near Yellow-Orange 16A.
Pistils: None observed.

OTHER CHARACTERISTICS

Disease resistance: No resistance nor susceptibility has been observed to pests and diseases of poinsettia crops.

Fruit/seed production: No seed observed.

What is claimed is:

1. A new and distinct cultivar of Poinsettia plant named 'ATN VR2' as herein illustrated and described.

* * * * *